United States Patent [19]

Norman

[11] Patent Number: 5,959,197
[45] Date of Patent: Sep. 28, 1999

[54] SYSTEM FOR DETERMINING FREE CEMENT CONTENT

[75] Inventor: Robert David Norman, Research Victoria, Australia

[73] Assignee: Thermo Crete Pty Ltd, Research Victoria, Australia

[21] Appl. No.: 08/894,580

[22] PCT Filed: Feb. 22, 1996

[86] PCT No.: PCT/AU96/00093

§ 371 Date: Nov. 12, 1997

§ 102(e) Date: Nov. 12, 1997

[87] PCT Pub. No.: WO96/26437

PCT Pub. Date: Aug. 29, 1996

[30] Foreign Application Priority Data

Feb. 24, 1995 [AU] Australia ................................ 13476/95

[51] Int. Cl.[6] .......................... G01N 25/00; G01N 15/06; B28C 7/04
[52] U.S. Cl. .............................. 73/61.76; 374/45; 366/17; 73/61.71
[58] Field of Search .................................. 73/866, 61.46, 73/61.65, 61.74, 61.76, 61.71; 374/102, 45; 210/167; 366/17

[56] References Cited

U.S. PATENT DOCUMENTS

| | | | |
|---|---|---|---|
| 3,897,928 | 8/1975 | Eisler | 249/78 |
| 3,997,434 | 12/1976 | Macauley, Jr. | 209/10 |
| 4,192,745 | 3/1980 | Hood | 106/713 |
| 4,488,815 | 12/1984 | Black | 366/8 |
| 4,588,299 | 5/1986 | Brown et al. | 366/8 |
| 4,715,726 | 12/1987 | Tsuruta | 374/102 |
| 5,209,130 | 5/1993 | Ohsaki et al. | 73/866 |
| 5,685,978 | 11/1997 | Petrick et al. | 210/241 |

Primary Examiner—Michael Brock
Assistant Examiner—Jay L. Politzer
Attorney, Agent, or Firm—Foley & Lardner

[57] ABSTRACT

A method and system for determining the free cement content of concrete plant waste water held in a pit or tank P in which the temperature of the water in the pit or tank and the temperature of water in a reference pit or tank $R_1$, is measured by thermocouples ($T_1$, $T_2$), the difference in temperature $\Delta T$ determined and used to calculate an estimate of the free cement in the waste water whereby the reduced amount of cement to be used in a concrete batching process (without compromising the strength of the concrete product) can be determined.

12 Claims, 1 Drawing Sheet

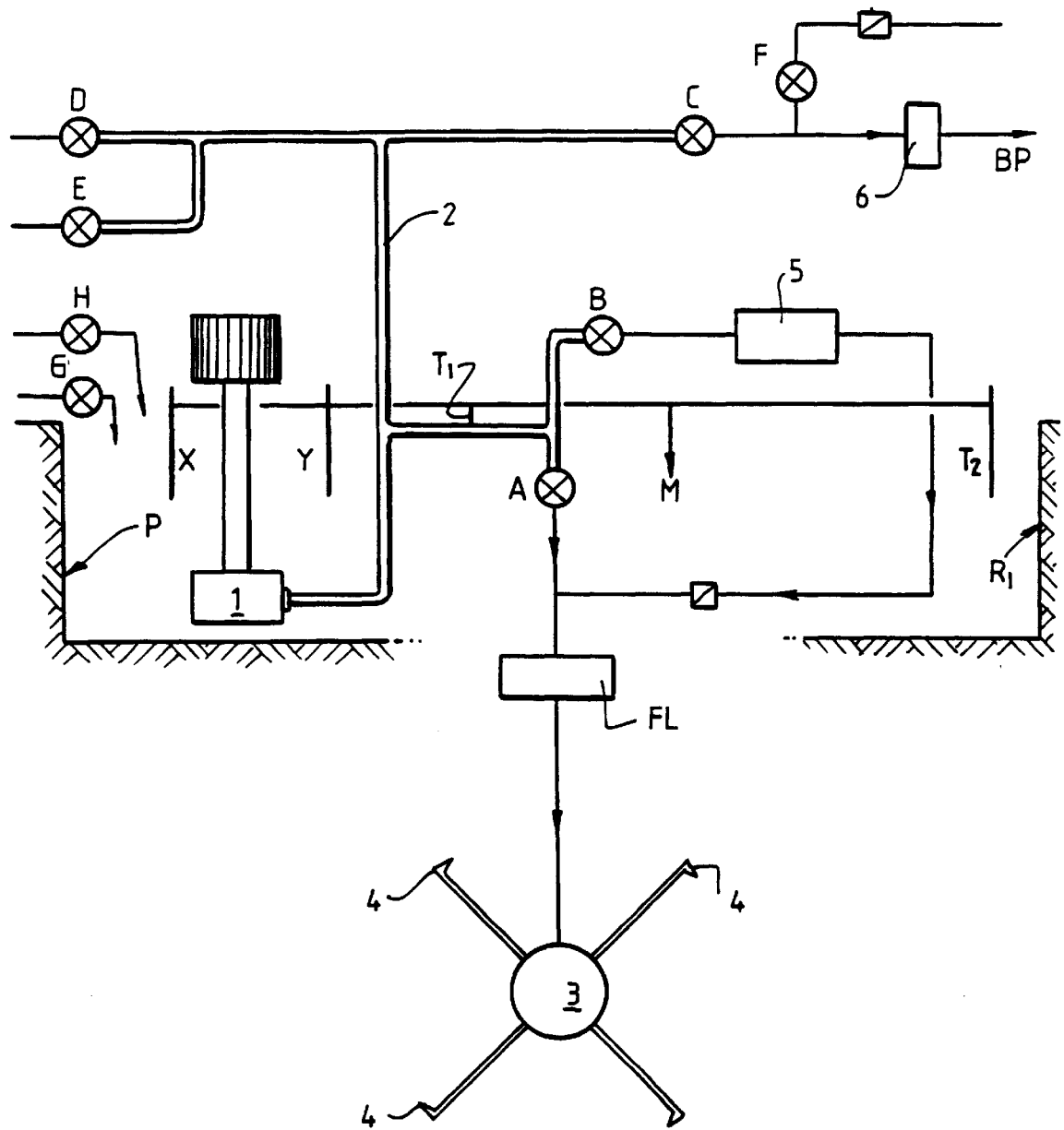

SYSTEM FOR DETERMINING FREE CEMENT CONTENT

FIELD OF THE INVENTION

This invention relates to a method for determining or estimating the free or available cement content in concrete plant waste water and to a system for performing the method to provide a measurement of the free cement content of a particular body of waste water.

BACKGROUND OF THE INVENTION

In our Australian Patent Application No 10247/92, we have described a system for recycling concrete plant waste water. The system consists of a central. high pressure pump which draws in the polluted water through a series of devices, where atmospheric air is injected into it. The aerated water is then returned to the pit via jet nozzles located around the floor. The thrust produced by these nozzles rotates the water around the pit, the movement resulting in the encapsulation of the semi-hydrated cement particles in the air bubbles. By the principle of buoyancy, these particles expand and rise towards the surface, the rotating water naturally vectoring them towards the central pump. This allows for their recirculation through the system, or their diversion through the batching water system, and subsequent re-use in concrete production. Water from the agitator pit is also used to wash out truck agitator barrels, this cement rich water then being returned to the agitator pit via an aggregate and sand collector box.

The amount of cement present in the pit at any one time bears no relation to it's volume in weight, but depends on what is termed the "activity factor". For example, after a weekend of no plant production, the pit would have a very low activity ratio, that is more cement particles in relation to volume of water.

Accordingly, to maximise the benefits from the agitation system described above, a method of measuring the free cement content of a particular volume of waste water would be most beneficial.

SUMMARY OF INVENTION AND OBJECTION

It is the object of the present invention to provide a method of determining or estimating the free cement content of concrete plant waste water in a simple but accurate manner which in turn allows the determination of the reduced amount of cement possible in a particular batch using the waste water while still producing a full strength concrete product.

The invention therefore provides a method of determining the free cement content of concrete plant waste water, comprising holding the waste water in a pit or tank, agitating the waste water to keep the solids in the waste water substantially in suspension, measuring the temperature of the waste water in said pit, measuring the temperature of water in a reference pit or tank, determining the difference in the measured temperatures, and using the temperature difference to calculate an estimate of the free cement in said waste water.

It has been found that the amount of cement saved R in kilograms is able to be calculated according to the following formula:

$$R = \frac{4.18 V^2 \Delta T}{300 v}$$

in which V is the volume of waste water under consideration, $\Delta T$ is the temperature difference referred to above and V is the volume of water in each concrete batch in liters per meter$^2$ of concrete.

If desired, an allowance is made for the temperature rise in the agitated pit due to the pumping activity and this value for a particular pit and pump combination is subtracted from the temperature difference in the above formula. The modified formula reads:

$$R = \frac{4.18 V^2 \Delta T - \Delta T_p}{300 v}$$

By determining the amount of free cement in the waste water, the amount of cement used in a batch of concrete prepared using part or all of the waste water can be correspondingly reduced in an accurate manner whereby the strength of the concrete product is not compromised while cost savings are still achieved.

The water in the reference pit may be clean water or polluted water but should not contain significant amounts of cementitious material, otherwise its ability to provide a proper reference will be somewhat compromised.

In another aspect, the invention provides a system for determining the free cement content of concrete plant waste water, comprising a waste water pit or tank for concrete plant waste water containing cementitious material, means for agitating the waste water in said pit or tank, a reference pit or tank containing water exposed to ambient conditions similar to the waste water pit or tank, temperature monitoring means in each pit or tank, means for determining the difference in the monitored temperatures, and means for utilising the temperature difference to calculate an estimate of the free cement in said waste water.

In a preferred form of the invention, the temperature difference is utilised in the above formula to calculate the cement saved by the use of the waste water containing cementitious material.

BRIEF DESCRIPTION OF THE DRAWINGS

The sole FIGURE of the drawings is a schematic representation of a concrete plant waste water recycling system embodying the invention.

DESCRIPTION OF THE PREFERRED EMBODIMENT

Referring to the drawing, the recycling system embodying the invention comprises a waste water storage and agitation pit P, a submerged agitator pump 1, such as a cantilever pump having no bearings or seals below the water line, which supplies high pressure cement slurry water to a high pressure distribution manifold 2 where it is available for the various services by way of electrically controlled valves A, B, C, D and E, which are controlled from the operator's control panel (not shown). The manifold 2 is connected to a known spoke-wheel manifold 3 via a filter F, with each spoke terminating in a jet nozzle 4 at predetermined positions within the pit P. An aerator 5 of any suitable construction, such as a known venturi device, is connected to the manifold 2 to introduce air bubbles into the recirculating water. By suitably positioning the jet nozzles 4 in the pit P, the waste water in the pit P is suitably agitated to substantially prevent or reduce the formation of sediments within the pit P. The air bubbles in the recirculated waste water are believed to operate to reduce gel coatings on the surface of the cement particles in the waste water to activate the particles as available cement in the concrete batching process.

Control switches at the truck washout points activate the valves E and D to supply washout water for the trucks. These valves operate through a time switch which is pre-set to give two to three minutes of washout water. Valve A is activated to the closed position when valves E or D are activated, to allow slurry water to be used in the batch system during washout. When the truck washout valves E or D or both are activated, make-up water from an above ground holding tank (not shown) will not enter the agitation pit P for a period of 10 to 15 minutes. This provides sufficient time for the washout waters to return to the agitation pit P to keep the water level constant. A make-up water valve G, is de-activated for the programmed time to achieve this. Valve H controls the supply of waste water to the pit P to maintain levels determined by a pit float (not shown).

The supply of slurry water to the batching plant B is controlled by a batch computer (not shown) which actuates valve C. A flow meter 6 monitors the volume of water supplied to the batching process. Valves A and B are activated to the closed position to produce a higher batch water flow rate. The batching plant B can comprise the hot water concrete batching plant described in Australian Patent Application No 20924/88, or any other plant capable of utilising waste water.

A flushing system is activated by the computer and must be selected by the operator at the completion of each days concrete production to prevent a slurry build-up in the batch delivery pipe. Valve F automatically supplies mains water to the delivery pipe to flush all of the cement slurry from the batch water supply pipe.

The agitation system is independent of the flushing system and does not need to operate when flushing. This dual provision enables the flushing system to be used as an alternative batching source should the central system fail.

Additionally, when the flushing valve F is activated this automatically operates the hot water blending valve into the cold position, allowing for the removal of slurry from the blend water system.

Valves A and B are programmed to give either water or water with air, at the jet nozzles located near the bottom of the agitation pit. The time cycle is preset to give the best motion for a particular pit size and shape.

A temperature sensor $T_1$, such as a suitable thermocouple or equivalent device, is positioned in the branch of manifold 2 that feeds into valves A and B, and a similar sensor $T_2$ is positioned in a reference tank or pit $R_1$ which contains a reference body of water, which may be fresh water, or polluted water, provided the reference water does not contain significant quantities of cementitious material. Since the sensor $T_1$ in the manifold 2 is exposed to high velocity waste water, it will be less likely to foul. The reference pit $R_1$ should hold approximately the same volume of water and should be exposed to the same ambient conditions as the waste water pit P so as to act as a reference in determining the temperature rise in the waste water pit P due to the hydration of cement. The temperatures of the respective bodies of waters in the waste water pit P and the reference tank $R_1$ are monitored and a temperature difference $\Delta T$ is determined, most conveniently by a microprocessor M associated with the concrete batching plant B.

The microprocessor M is programmed to utilise the temperature difference $\Delta T$ to calculate a cement saving value R associated with the use of the waste water contained in the waste water pit P. The microprocessor is programmed for each concrete batching site to take into consideration the volume of waste water held in the pit P and other factors which are discussed further below. If desired the algorithm can include an allowance for the small dynamic temperature rise in the waste water due to its high velocity in the manifold 2.

For a waste water pit holding approximately 14000 liters, the temperature rise due to hydration of cement is as follows:

$$Q=4.18 \times V \times 10^3 \times \Delta T$$

in which:

Q=heat of hydration of cement=300×C×1000 joules.

C=kilograms of equivalent cement

V=volume of pit liters×$10^3$ grams so:

$$Q=4.18 \times V \times 10^3 \times \Delta T=300 \times C=10^3$$

therefore:

$$C = \frac{4.18 \times 14000 \times 10^3 \times \Delta T}{300 \times 10^3}$$

C=195.07 $\Delta T$ kg of equivalent cement in the 14000 liter pit

Assuming a concrete batch involves the use of about 100 liters per $M^2$ of concrete, the free cement or equivalent cement per load $$R = \frac{C}{\left(\frac{100}{14000}\right)}$$

$$R = \frac{C}{140}$$

$$C = 140R$$

Substituting this into the equation for C given above:

140 R=195.07 $\Delta T$ therefore:

$$R = \frac{195.07 \Delta T}{140}$$

$$R = 1.393 \Delta T$$

An allowance for the temperature rise due to pump activity in the agitation pit P can be calculated as follows:

Assuming an 11 kW pump having a heat output of 29.5MJ per hour, the temperature rise due to the pump $$\Delta T_p = \frac{Q}{4.18 \times V \times 10^3}$$

$$= \frac{29.5 \times 10^6}{4.18 \times 14000 \times 10^3}$$

therefore: $\Delta T_p = 0.5°$ C.

therefore:

$R = 1.393(\Delta T - 0.5)$

The output from each thermocouple T is in millivolts and $\Delta T$ can therefore be represented as $$\Delta T = \frac{mV}{50}$$

therefore:

$R = 0.0279 \times mV - 0.5$.

In this way, the difference in voltage outputs from the respective thermocouples can be used directly to provide a value of the free cement or equivalent cement per load which can be directly used by the microprocessor M controlling the batching operation to control the amount of cement used in a concrete batch prepared using the waste water in the pit P, without any material loss in the strength of the concrete produced.

A suitable photoelectric measuring device is immersed in the waste water in pit P to continuously measure the solids content or solids ratio of the waste water in the pit P. This measurement is relayed to the microprocessor M and is used to automatically control the amount of water used in each batch to compensate for the solids introduced by the waste water.

The pH of the waste water is also monitored, by a known pH meter Y, to ensure that low quality waste water having an unacceptably high pH (say above 11) is not used in the batching plant B.

Significant savings can be achieved by using the above described method and system embodying the invention. Test results have shown that a recovery of approximately 10 kg of cement per cubic meter of concrete production is possible, and since the target strength of the batched concrete is not affected as a result of the relatively accurate measurement of the free cement available in the waste water pit P, the savings should be able to be maintained. In fact independent tests have shown that a concrete batch using waste water from the pit P has a superior strength development at 28 days than a concrete batch using fresh batch water.

It will be appreciated that different formulae or algorithms for calculating the free cement equivalent of the waste water can be used to produce results similar to those described above. Similarly, the equivalent cement can be separately calculated for each concrete batch and waste water supply and the batching plant operation manually changed to reduce the amount of cement used in the batch.

I claim:

1. A method of determining the free cement content of concrete plant waste water, comprising holding the waste water in a pit or tank, agitating the waste water to keep the solids in the waste water substantially in suspension, measuring the temperature of the waste water in said pit, measuring the temperature of water in a reference pit or tank, determining the difference in the measured temperatures, and using the temperature difference to calculate an estimate of the free cement in said waste water.

2. The method of claim 1, wherein the temperature difference $\Delta T$ is applied to the formula:

$$R = \frac{4.18 V^2 \Delta T}{300 v}$$

in which V is the volume of waste water under consideration, $\Delta T$ is the temperature difference referred to above and V is the volume of water in each concrete batch in liters per meter$^2$ of concrete.

3. The method of claim 2, further comprising monitoring the solids content of the waste water in said pit and using this data to control the water content of the concrete being prepared in the concrete plant.

4. The method of claim 1, further comprising monitoring the solids content of the waste water in said pit and using this data to control the water content of the concrete being prepared in the concrete plant.

5. The method of claim 2, wherein the amount of cement saved R is calculated by the formula:

$$R = \frac{4.18 V^2 (\Delta T - \Delta T_p)}{300 v}$$

wherein $\Delta T_p$ is the temperature rise due to pumping.

6. The method of claim 5, further comprising monitoring the solids content of the waste water in said pit and using this data to control the water content of the concrete being prepared in the concrete plant.

7. A system for determining the free cement content of concrete plant waste water, comprising a waste water pit or tank for concrete plant waste water containing cementitious material, means for agitating the waste water in said pit or tank, a reference pit or tank containing water exposed to ambient conditions similar to the waste water pit or tank, temperature monitoring means in each pit or tank, means for determining the difference in the monitored temperatures, and means for utilising the temperature difference to calculate an estimate of the free cement in said waste water.

8. The system of any claim 7, further comprising means for monitoring the solids content of the waste water in said pit and for using this data to control the water content of the concrete being prepared in the concrete plant.

9. The system of claim 7, wherein the temperature difference $\Delta T$ is applied to the formula:

$$R = \frac{4.18 V^2 \Delta T}{300 v}$$

in which V is the volume of waste water under consideration, $\Delta T$ is the temperature difference referred to above and V is the volume of water in each concrete batch in liters per meter$^3$ of concrete.

10. The method of claim 9, further comprising means for monitoring the solids content of the waste water in said pit and for using this data to control the water content of the concrete being prepared in the concrete plant.

11. The system of claim 9, wherein the amount of cement saved R is calculated by the formula:

$$R = \frac{4.18 V^2 (\Delta T - \Delta T_p)}{300 v}$$

wherein $\Delta T_p$ is the temperature rise due to pumping.

12. The method of claim 11, further comprising means for monitoring the solids content of the waste water in said pit and for using this data to control the water content of the concrete being prepared in the concrete plant.

* * * * *